(12) United States Patent
Huynh et al.

(10) Patent No.: US 8,366,769 B2
(45) Date of Patent: Feb. 5, 2013

(54) LOW-PROFILE, PIVOTABLE HEART VALVE SEWING RING

(75) Inventors: Van Le Huynh, Irvine, CA (US); Michael J. Scott, Lake Forest, CA (US); Derrick Johnson, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 2155 days.

(21) Appl. No.: 10/802,314

(22) Filed: Mar. 17, 2004

(65) Prior Publication Data
US 2004/0176839 A1    Sep. 9, 2004

Related U.S. Application Data

(63) Continuation of application No. 09/585,098, filed on Jun. 1, 2000, now abandoned.

(51) Int. Cl.
*A61F 2/24* (2006.01)
(52) U.S. Cl. ...................................................... 623/2.41
(58) Field of Classification Search ................. 623/1.11, 623/1.24, 1.26, 2.11, 2.14–2.16, 2.18, 2.4, 623/2.41
See application file for complete search history.

(56) References Cited

U.S. PATENT DOCUMENTS

| | | |
|---|---|---|
| 3,781,969 A | 1/1974 | Anderson |
| 3,839,741 A | 10/1974 | Haller |
| 4,084,268 A | 4/1978 | Ionescu et al. |
| 4,197,593 A | 4/1980 | Kaster et al. |
| 4,345,340 A | 8/1982 | Rosen |
| 4,477,930 A | 10/1984 | Totten et al. |
| 4,535,483 A | 8/1985 | Klawitter et al. |
| 4,605,407 A | 8/1986 | Black et al. |
| 4,626,255 A | 12/1986 | Reichart et al. |
| 4,680,031 A | 7/1987 | Alonso |
| 4,705,516 A | 11/1987 | Barone et al. |
| 4,816,029 A | 3/1989 | Penny, III et al. |
| 4,863,460 A | 9/1989 | Magladry |
| 4,865,600 A | 9/1989 | Carpentier et al. |

(Continued)

FOREIGN PATENT DOCUMENTS

| | | |
|---|---|---|
| EP | 0 070 259 | 6/1982 |
| EP | 0 075 530 B1 | 9/1982 |

(Continued)

OTHER PUBLICATIONS

Carpentier, "Implant Technique for the Aortic Carpentier-Edwards SAV Bioprosthesis" Chief, Department of Cardiovascular Surgery Hopital Broussais Paris, France.

(Continued)

*Primary Examiner* — Brian Pellegrino
(74) *Attorney, Agent, or Firm* — AnneMarie Kaiser; Guy Cumberbatch

(57) ABSTRACT

A sewing ring for prosthetic heart valves that is connected and configured to pivot outward. A biocompatible fabric covering surrounds at least a portion of the sewing ring, and the ring may be exclusively connected to a stent with the fabric. The sewing ring may be generally planar and of uniform thickness, or may be of varying thickness. The fabric may be used to encompass both the stent and the sewing ring, and may be a single piece. A seam may be provided in the fabric as a discrete pivoting line. The sewing ring may be convertible between bi-stable positions. The ring may extend outward in a frusto-conical shape so as to enable inversion between a position facing the inflow end of the valve and a position facing the outflow end of the valve. The sewing ring may have a compliant insert having a celled construction defined by outer walls and inner ribs. A method of implantation, and a method of assembly of the heart valve is also provided.

21 Claims, 14 Drawing Sheets

U.S. PATENT DOCUMENTS

| | | | |
|---|---|---|---|
| 4,865,870 | A | 9/1989 | Hu et al. |
| 4,892,540 | A | 1/1990 | Vallana |
| 5,035,709 | A | 7/1991 | Wieting et al. |
| 5,071,431 | A | 12/1991 | Sauter et al. |
| 5,072,431 | A | 12/1991 | Ohmori et al. |
| 5,104,406 | A | 4/1992 | Curcio et al. |
| 5,147,391 | A | 9/1992 | Lane |
| 5,178,633 | A | 1/1993 | Peters |
| 5,243,330 | A | 9/1993 | Thuillard |
| 5,258,023 | A | 11/1993 | Reger |
| 5,354,330 | A | 10/1994 | Hanson et al. |
| 5,360,014 | A | 11/1994 | Sauter et al. |
| 5,370,684 | A | 12/1994 | Vallana et al. |
| 5,397,346 | A | 3/1995 | Walker et al. |
| 5,397,348 | A | 3/1995 | Campbell et al. |
| 5,480,425 | A | 1/1996 | Ogilive |
| 5,487,760 | A | 1/1996 | Villafana |
| 5,571,175 | A | 11/1996 | Vanney et al. |
| 5,607,470 | A | 3/1997 | Milo |
| 5,755,783 | A | 5/1998 | Stobie et al. |
| 5,766,240 | A | 6/1998 | Johnson |
| 5,824,069 | A | 10/1998 | Lemole |
| 5,843,179 | A | 12/1998 | Vanney et al. |
| 5,855,603 | A | 1/1999 | Reif |
| 5,876,436 | A | 3/1999 | Vanney et al. |
| 5,928,281 | A | 7/1999 | Huynh et al. |
| 6,045,576 | A | 4/2000 | Starr et al. |

FOREIGN PATENT DOCUMENTS

| | | |
|---|---|---|
| EP | 0 119 357 | 12/1983 |
| EP | 0 200 926 | 4/1986 |
| EP | 0 350 302 | 7/1989 |
| EP | 0 541 215 | 5/1993 |
| WO | WO 82/02829 | 9/1982 |
| WO | WO 92/19184 | 11/1992 |
| WO | WO 93/20781 | 10/1993 |
| WO | WO 94/01060 | 1/1994 |
| WO | WO 95/16408 | 6/1995 |
| WO | WO 95/28899 | 11/1995 |
| WO | WO 01/12105 A1 | 2/2001 |

OTHER PUBLICATIONS

"Judge Our Pericardial Valve by Its Appearance and You Will Only Get Half the Picture" Baxter.

Canadian search letter for Application No. 2,461,531: Dec. 2007.

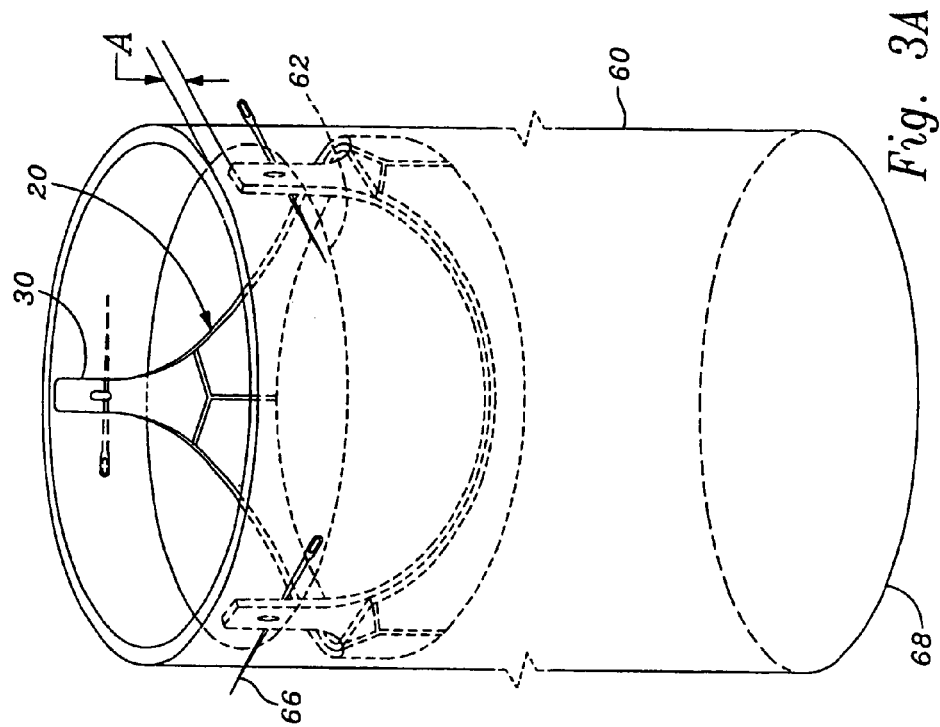
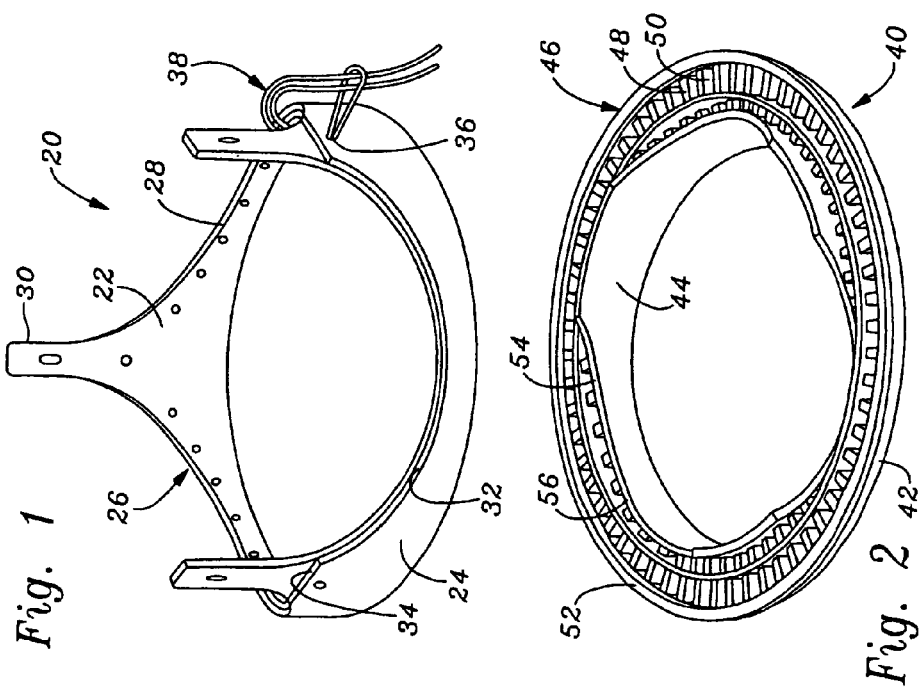

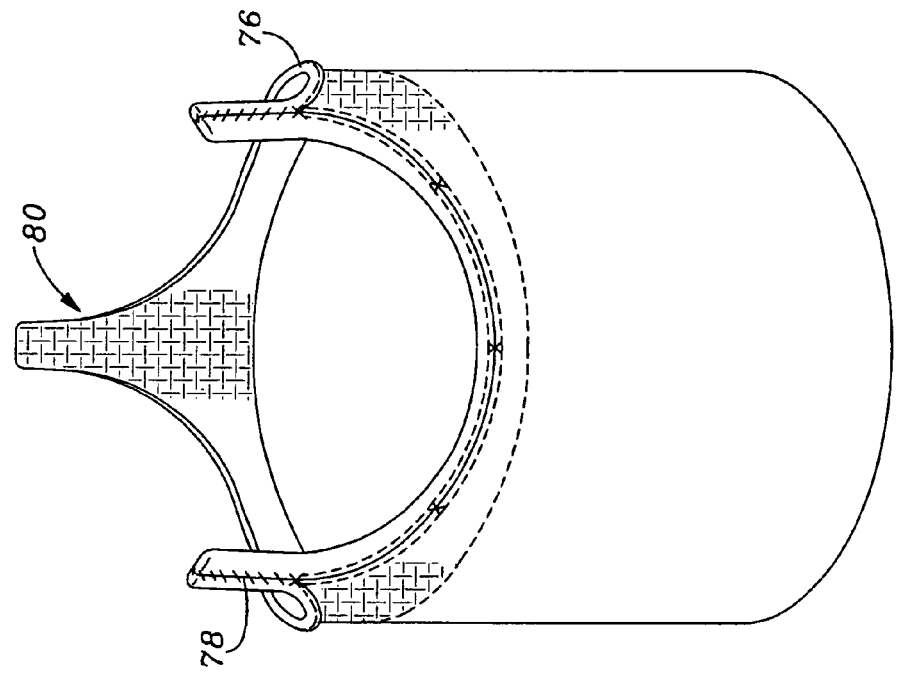
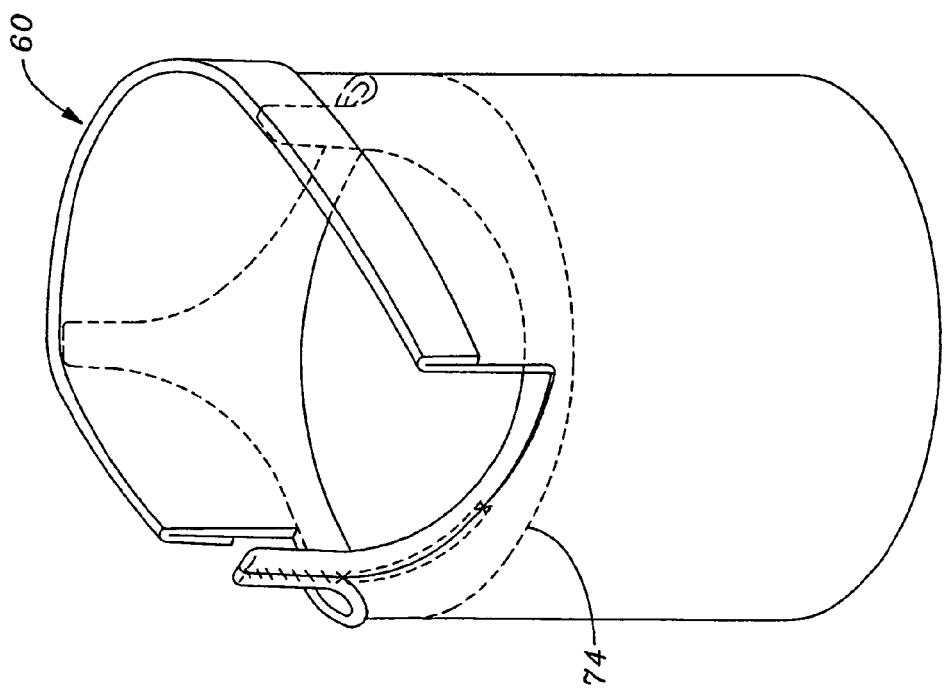

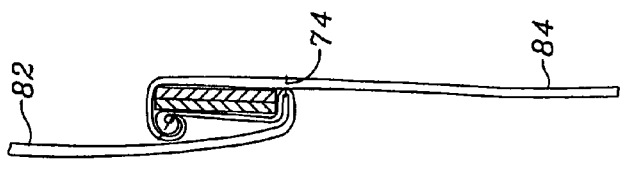
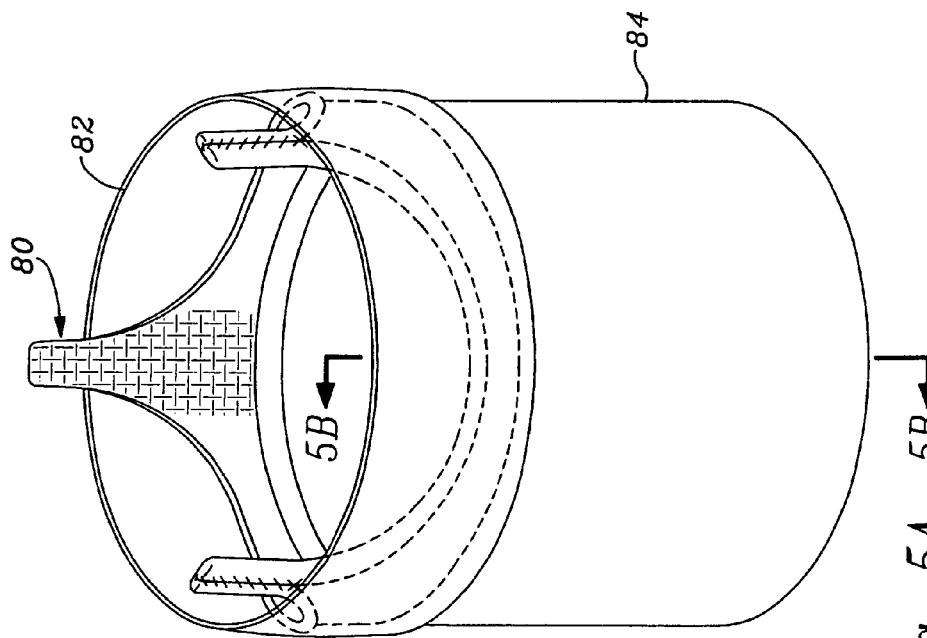
Fig. 5B
Fig. 5A

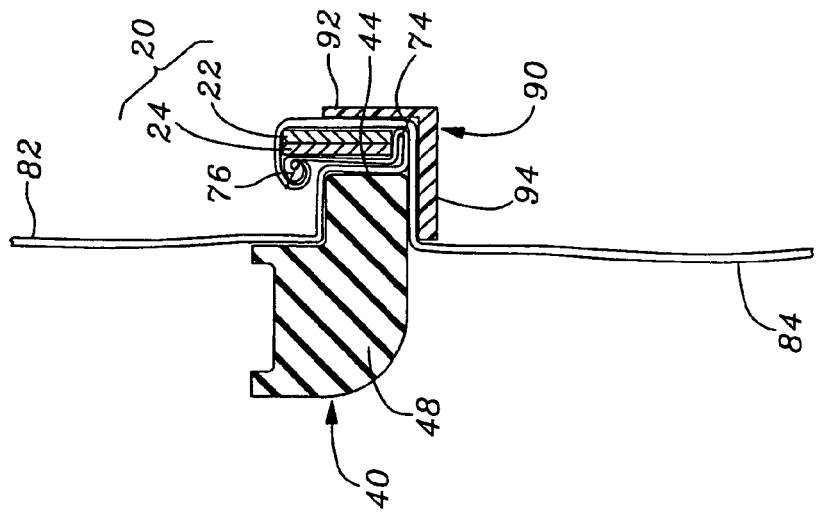
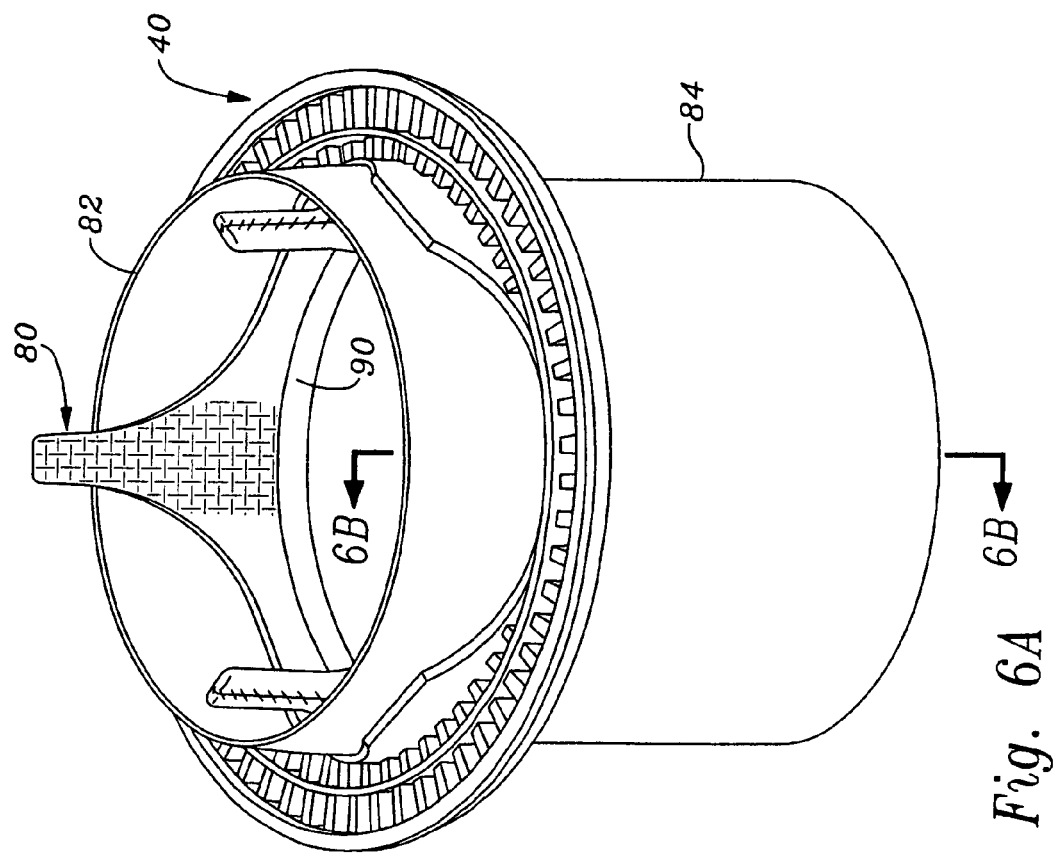

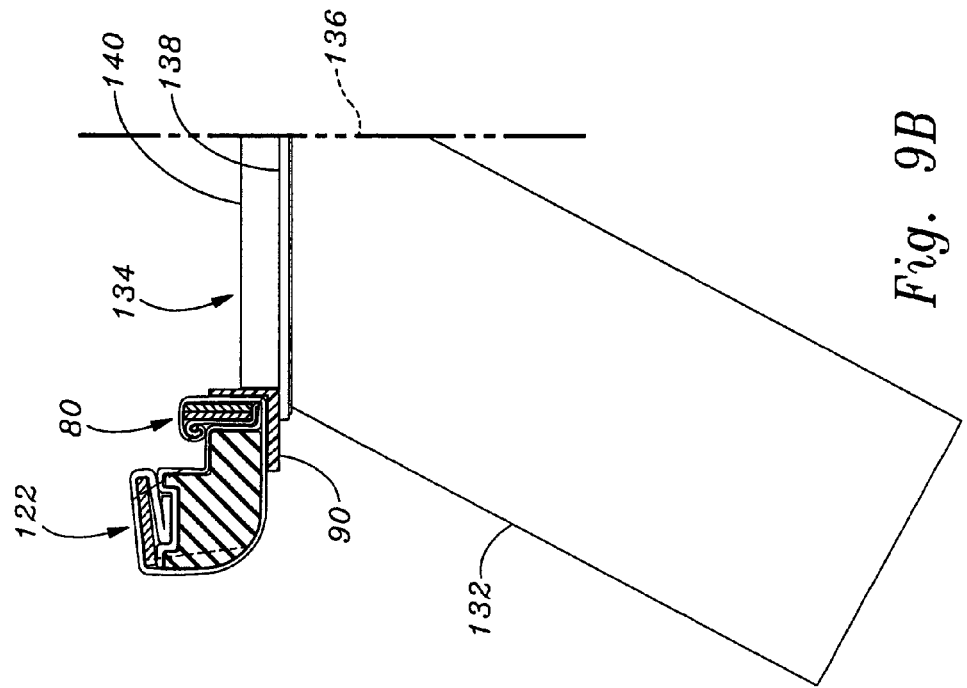
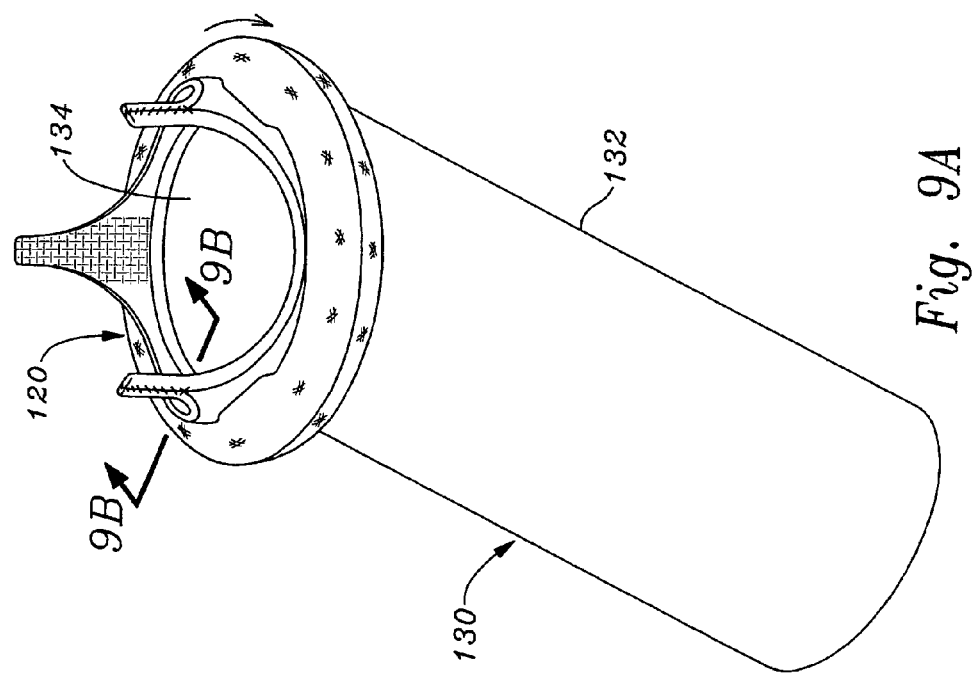

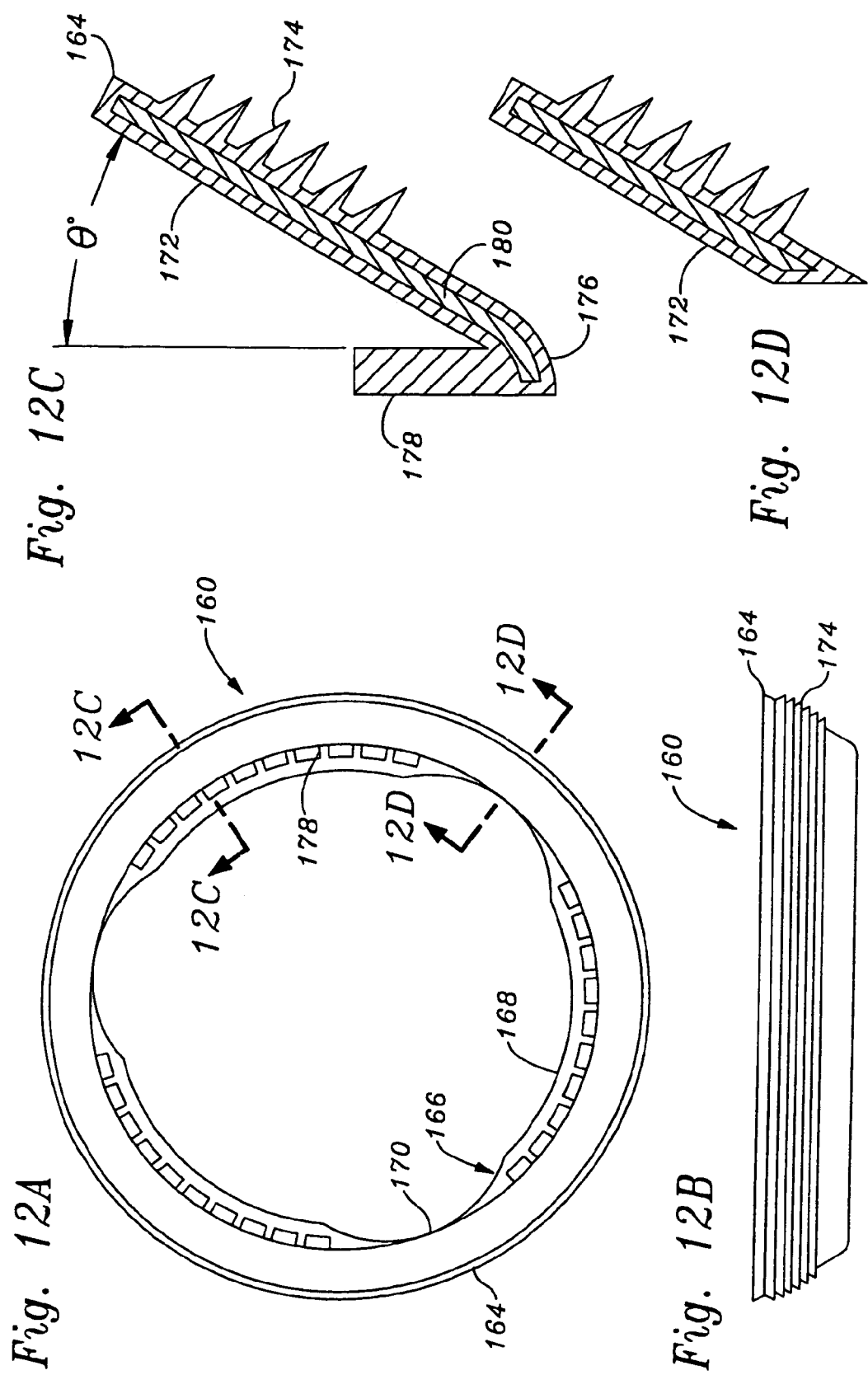

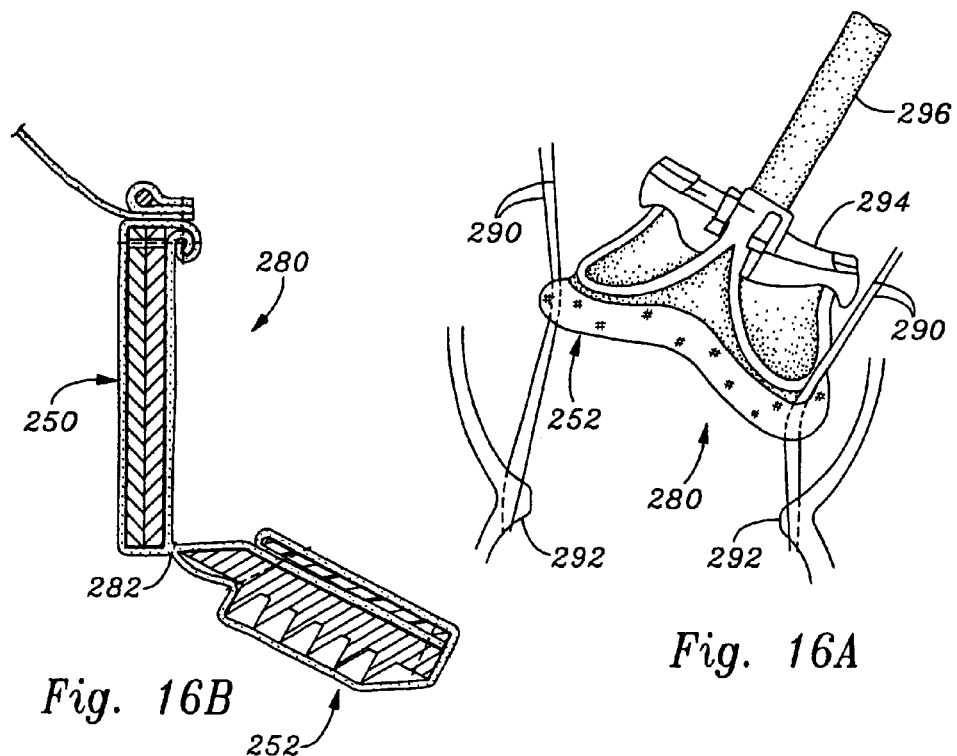
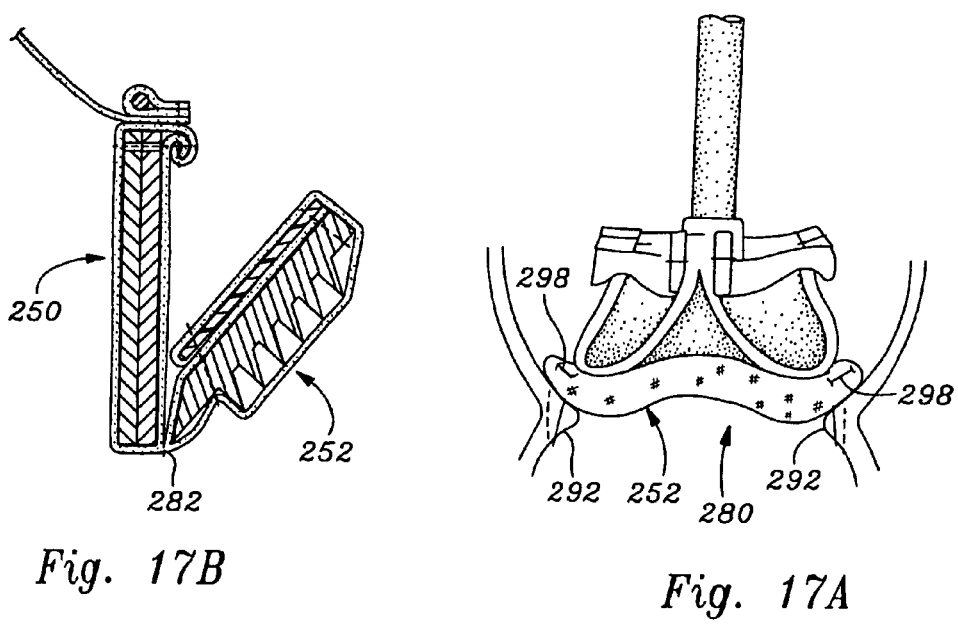

LOW-PROFILE, PIVOTABLE HEART VALVE SEWING RING

RELATED APPLICATIONS

The present application is a continuation of Ser. No. 09/585,098, filed on Jun. 1, 2000 now abandoned, entitled LOW PROFILE HEART VALVE SEWING RINGS.

FIELD OF THE INVENTION

The present invention relates generally to medical devices and particularly to heart valve prostheses having a low-profile sewing ring that enables larger valve orifices to be used.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve's, imitating the natural action of the flexible heart valve leaflets which seal against each other to ensure the one-way blood flow. In both types of prosthetic valves, a biocompatible fabric-covered suture or sewing ring or cuff on the valve body (mechanical) or stent (tissue-type) provides a platform for attaching the valve to the annulus of the particular valve being replaced.

The valves of the heart separate chambers therein, and are each mounted in an annulus therebetween. The annuluses comprise dense fibrous rings attached either directly or indirectly to the atrial and ventricular muscle fibers. In a valve replacement operation, the damaged leaflets are excised and the annulus sculpted to receive a replacement valve. Ideally the annulus presents relatively healthy tissue that can be formed by the surgeon into a uniform ledge projecting into the orifice left by the removed valve. The time and spacial constraints imposed by surgery, however, often dictate that the shape of the resulting annulus is less than perfect for attachment of a sewing ring. Moreover, the annulus may be calcified as well as the leaflets and complete annular debridement, or removal of the hardened tissue, results in a larger orifice and less defined annulus ledge to which to attach the sewing ring. In short, the contours of the resulting annulus vary widely after the natural valve has been excised.

Conventional placement of the valve is intra-annular, with the valve body deep within the narrowest portion of the annulus to enhance any seal effected by the sewing ring/suture combination and reduce the chance of perivalvular leakage. Surgeons report using at least 30 simple sutures or 20 mattress-type sutures to prevent leakage. Mattress sutures are more time consuming and essentially comprise double passes of the needle through the tissue with one knot.

Naturally, the implantation of a prosthetic heart valve, either a mechanical valve or a bioprosthetic valve (i.e., "tissue" valve), requires a great deal of skill and concentration given the delicate nature of the native heart tissue, the spatial constraints of the surgical field and the criticality of achieving a secure and reliable implantation. It is of equal importance that the valve itself has characteristics that promote a long valve life and that have minimal impact on the physiological makeup of the heart environment.

In view of the foregoing, it is evident that an improved sewing ring that addresses the apparent deficiencies in existing sewing rings is necessary and desired. That is, there is a need for a sewing ring that increases the orifice area of the valve while at the same time simplifying the fabrication and implantation steps.

SUMMARY OF THE INVENTION

The present invention provides an improved sewing ring and sewing ring/stent assembly that facilitates manufacture and implantation of heart valves. The sewing ring is adapted to pivot or move outward from the stent, thus enabling a surgeon during the implantation procedure to more easily isolate the sewing ring against the native tissue and away from the stent and tissue leaflets. Thus, there is less chance of the surgeon puncturing the leaflets. Furthermore, the compliance of the sewing ring, or ability to pivot the ring away from the stent, enables the sewing ring to be made smaller in the radial dimension, and thus the overall valve orifice size can be increased. Additionally, the manufacturing process is facilitated because various regions around the stent can be more easily visualized and accessed by virtue of the movable sewing ring.

In one aspect, the present invention provides a sewing ring attached to a generally annular periphery of a heart valve. The sewing ring includes a suture-permeable ring attached to the heart valve periphery and configured to pivot from a first position substantially adjacent the periphery to a second position outward from the first position. The sewing ring desirably comprises a suture-permeable insert ring and a fabric cover. The insert ring may be substantially planar. The fabric covering the insert ring also desirably covers a portion of the heart valve. Moreover, the fabric covering both the insert ring and a portion of heart valve also preferably connects the ring to the heart valve periphery. A seam may be provided wherein the sewing ring pivots between the first and second positions about the seam. In one embodiment, the first and second positions are stable such that the sewing ring is bi-stable.

In a further aspect, a heart valve having an inflow end and an outflow end is provided, comprising a generally annular stent, and a suture-permeable sewing ring attached to a periphery thereof. The sewing ring is movable between two positions, wherein in the first position the sewing ring extends generally toward the outflow end of the valve and in the second position the sewing ring extends generally toward the inflow end of the valve. The sewing ring may comprise an insert ring and a fabric cover, and the fabric covering the insert ring may also cover a portion of the stent. In a preferred embodiment, the sewing ring attaches to the stent exclusively with a portion of a fabric that also covers a portion of the sewing ring. A seam is desirably provided in the fabric at the line of attachment between the sewing ring and the stent, wherein the sewing ring pivots about the seam between the first and second positions. The first and second positions may be stable, and the insert ring may be frustoconical in shape such that in the first position the ring extends toward the outflow end and in the second position the ring extends toward the inflow end. Furthermore, the insert ring may be provided with alternating radially thick and thin regions, or it may have a radially unulating shape, to facilitate movement between the first and second positions.

In another aspect, the present invention provides a heart valve including a generally annular stent having a periphery, a tubular fabric, and a generally annular suture-permeable insert sized at least as large as the stent periphery. The stent and insert are connected together exclusively by a portion of the fabric that permits relative outward pivoting of the insert with respect to the stent. In a preferred embodiment, the fabric at least partly covers both the stent and insert. A seam may be provided in the fabric at the line of attachment between the insert and the stent to provide a discrete pivot line. In a preferred embodiment, the tubular fabric is a single piece prior to assembly of heart valve, and desirably encompasses both the stent and insert. The stent may have an undulating outflow edge comprising alternating commissures and cusps, wherein the fabric covers the outflow edge. The insert is desirably disposed around stent to pivot about the outer surface thereof, and a sewing tab along the undulating outflow edge is desirably sewn directly to the stent to prevent relative movement of the fabric upon pivoting of the insert.

In a further embodiment, a method of implanting a heart valve in host tissue (e.g., an aortic annulus) is provided. The heart valve has an inflow end and an outflow end, and a sewing ring attached to a periphery thereof. The method includes positioning the sewing ring to extend generally toward the inflow end of the valve, attaching the sewing ring to the host tissue, and re-positioning the valve with respect to the attached sewing ring so that the sewing ring extends generally toward the outflow end of the valve. The method of attachment preferably comprises suturing. The method also may include providing the heart valve having a stent and a plurality of leaflets supported thereby, the sewing ring being located substantially adjacent the valve when extending generally toward the inflow end of the valve. The method of re-positioning may thus include inverting the sewing ring by pivoting it outward from the position substantially adjacent the valve. In one embodiment, the sewing ring is configured and attached to the stent so as to be bi-stable between the two positions.

Further, the present invention provides a method of assembling a heart valve, including providing a generally annular stent having a periphery, a tubular fabric, and a generally annular suture-permeable insert ring sized at least as large as the stent periphery. The method includes connecting the stent and insert ring with the fabric to permit relative outward pivoting of the fabric-covered insert ring with respect to the stent. The method may include completely covering the stent with the tubular fabric prior to connecting the insert ring with the fabric. Furthermore, the tubular fabric preferably consists of a single piece, wherein the method includes covering both the stent and the insert ring with the single piece. The method further may include holding a portion of tubular fabric against the annular stent using an assembly fixture. The assembly fixture desirably comprises an annular member and is mounted for rotation about an assembly handle. The handle has an elongated grip, wherein the axis of rotation of the assembly fixture is angled with respect to the grip.

A further understanding of the nature and advantages of the invention will become apparent by reference to the remaining portions of the specification and drawings.

BRIEF DESCRIPTION OF THE DRAWINGS

FIG. 1 is a perspective view of a stent assembly used in an exemplary mitral or pulmonary position heart valve of the present invention;

FIG. 2 is a perspective view of a suture-permeable insert for an exemplary mitral or pulmonary position heart valve sewing ring of the present invention;

FIGS. 3A and 3B are perspective views of initial steps in an assembly process of a heart valve of the present invention wherein a tubular fabric covering is wrapped around the stent assembly of FIG. 1;

FIG. 3C is a cross-sectional view taken along line 3C-3C of FIG. 3B;

FIGS. 4A and 4B are perspective views of further steps in the heart valve assembly process in which the fabric covering is attached along the outflow edge of the stent assembly;

FIG. 5A is a perspective view of a further step in the heart valve assembly process in which free edges of the tubular fabric covering are created in preparation for addition of the insert shown in FIG. 2;

FIG. 5B is a cross-sectional view taken along line 5B-5B of FIG. 5A;

FIG. 6A is a perspective view of a further step in the heart valve assembly process wherein the insert of FIG. 2 is positioned around the stent assembly of FIG. 1, with the fabric covering therebetween, and with the help of an assembly fixture;

FIG. 6B is a cross-sectional view taken along line 6B-6B of FIG. 6A;

FIG. 9A is a perspective view of the subassembly of FIG. 8A mounted on a final assembly handle of the present invention;

FIG. 9B is a partial sectional view of the subassembly taken along line 9B-9B of FIG. 9A and mounted on the final assembly handle;

FIGS. 12A-12D are various views of a suture-permeable insert for the sewing ring of the subassembly of the exemplary heart valve seen in FIGS. 11A-11C;

FIGS. 16A and 16B are an elevational view and cross-section, respectively, of a valve having the stent/sewing ring subassembly of FIG. 14 during an attachment step of implantation; and FIGS. 17A and 17B are an elevational view and cross-section, respectively, of a valve having the stent/sewing ring subassembly of FIG. 14 during a seating step of implantation.

DESCRIPTION OF THE PREFERRED EMBODIMENTS

Figures 3B, 3C:
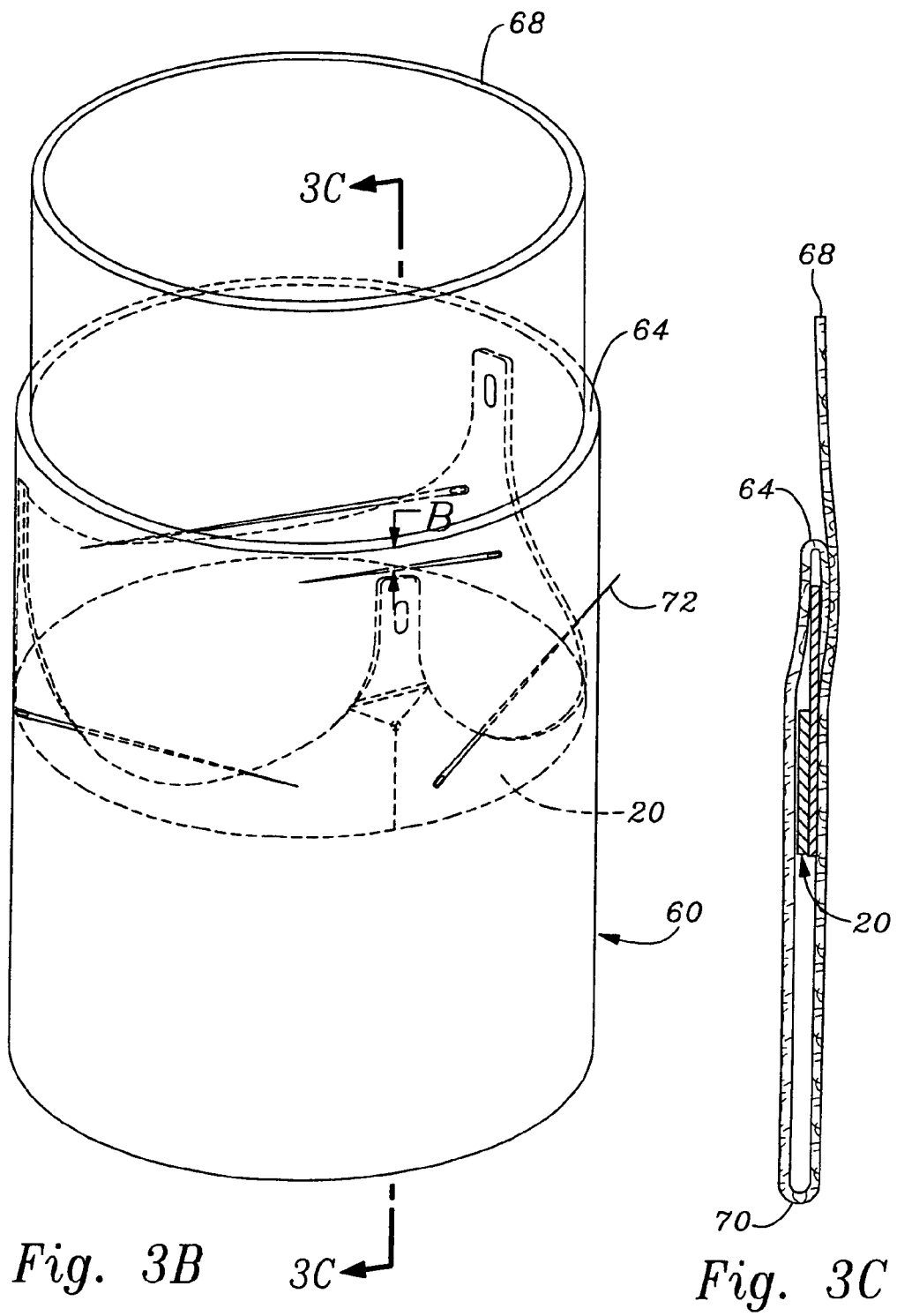

The present invention provides an improved heart valve sewing ring that enables an increase in the effective orifice size of the valve without increasing the overall valve outer diameter. Sewing rings for a mitral heart valve and an aortic heart valve are illustrated herein, but those of skill in the art will understand that many of the inventive concepts are applicable to heart valves for the pulmonary or tricuspid valve positions. More specifically, the annulus for the mitral and tricuspid positions are generally planar and non-scalloped, while the annulus for the aortic and pulmonary positions are generally scalloped or undulating (i.e., three dimensional). Therefore, certain sewing ring features disclosed herein may be more or less suitable to a planar or scalloped annulus. Moreover, although certain features are described as particularly suited to either the mitral (planar annulus) or aortic (scalloped annulus) valve designs, such features in other constructions may be applicable to both valve designs. Finally, although various materials and dimensions maybe described as preferred herein, other materials and dimensions may work equally well and are not necessarily excluded.

The present invention also describes various steps in the assembly process of heart valves to form the sewing rings of the present invention. It should be understood that the assembly steps may be accomplished in a different order, and an assembly process in accordance with the present invention may not include all of the steps described and illustrated herein. Furthermore, additional steps in the assembly process may be included other than those specifically disclosed.

FIGS. 1 and 2 illustrate two components of a tissue-type heart valve of the present invention for use in a non-scalloped annulus (i.e., mitral or tricuspid). Specifically, FIG. 1 illustrates a stent assembly 20 comprising an annular, flexible, inner member 22, and an annular, outer member 24 that is relatively less flexible than the inner member. Both the inner member 22 and the outer member 24 are desirably formed as thin-walled bands that contact one another at their facing surfaces. The inner member 22 includes an outflow edge 26 that alternates between curvilinear cusps 28 and upstanding commissures 30.

The stent assembly 20 is used in the construction of a tri-leaflet heart valve, wherein three bio-prosthetic leaflets are suspended within the valve orifice and are attached around the valve generally along the outflow edge 26 of the inner member 22. In other valves that could be constructed in accordance with present invention, more or less than three leaflets may be utilized, with the number of cusps 28 and commissures 30 varying accordingly.

The outer member 24 also includes an outflow edge that includes curvilinear cusps 32 juxtaposed with the cusps 28 of the inner member 22. Instead of continuing upward at the commissures, however, the outer member 24 terminates at straight edges 34 rendering the commissures 30 of the inner member 22 unsupported, and therefore highly flexible. In a preferred embodiment, the inner member 22 is formed of a polymer, preferably MYLAR, while the outer member 24 is relatively more rigid, and may be a biocompatible metal such as ELGILOY.

The inner member 22 is secured to the outer member 24 via a plurality of through holes 36 and attachments sutures 38. In other embodiments, the stent assembly 20 maybe formed of a single member, or the members 22, 24 may be fastened together using adhesive or other suitable means.

FIG. 2 illustrates an exemplary suture-permeable sewing ring insert 40 used in the construction of the mitral heart valve of the present invention. The insert 40 is generally annular and includes a solid, preferably curvilinear inflow surface 42, a solid, generally tubular inner wall 44, and an open-celled outflow face 46. The insert 40 may be molded of a biocompatible material such as silicone rubber, and includes a plurality of internal ribs 48 defining voids 50 therebetween to make up the open-celled construction. An outer edge 52 of the outflow face 46 is desirably circular, and in one plane, while the inner edge 54 (formed by the outflow edge of the inner wall 44) includes a series of depressions 56; specifically three, in accordance with the tri-leaflet design of the illustrated heart valve. The depressions 56 receive cusp portions of a wireform of a heart valve and help prevent axial movement of the wireform and leaflets with respect to the sewing ring. Such construction is shown and described in U.S. Pat. No. 5,928,281, issued Jul. 27, 1999, which disclosure is hereby expressly incorporated by reference. Because the valve position for which the sewing ring insert 40 is useful is non-scalloped, the insert 40 is substantially planar. Furthermore, the exemplary insert 40 is of uniform thickness about its circumference, although non-uniform configurations are possible.

FIGS. 3A-3C illustrate initial steps in an assembly process for the mitral heart valve of present invention in which a tubular fabric covering 60 is draped over the stent assembly 20. The fabric covering 60 may be a variety of materials, but is typically a polyester such as polyethylene terepthalate. In FIG. 3A, the tubular fabric covering 60 is shown around the outside of the stent assembly 20 with an upper edge 62 folded down and in so as to be radially inside the upper ends of the commissures 30. A fold line 64 is disposed a distance A above the tips of the commissures 30, which distance is desirably about 1 mm. A plurality of pins 66 or other such temporary fixation devices are utilized to maintain the relative position of the fabric covering 60 in this folded configuration.

FIGS. 3B and 3C show a subsequent step in the attachment of the stent assembly 20 and the fabric covering 60 wherein the lower edge 68 seen in FIG. 3A has been folded inward and pulled upward through the middle of the stent assembly to be disposed above the fold line 64. The lower edge of the fabric covering 60 is thus defined by a second fold line 70 disposed some distance below the stent assembly 20. Again, a plurality of pins 72 may be used to temporarily hold the relative positions of the stent assembly 20 and fabric covering 60.

At this stage, as seen in FIGS. 4A and 4B, a backstitch seam 74 is added below the stent assembly 20 to join the inner and outer tubular portions of fabric covering 60. The backstitch seam 74 is more clearly shown in the cross-section of FIG. 5B. FIGS. 4A and 4B schematically illustrate a conventional process of trimming and sewing the upper portions of the fabric covering 60 so as to form a rolled fabric sewing tab 76 along the upper edge of the stent assembly 20. Specifically, the sewing tab 76 extends generally outward from the stent assembly 20 and comprises several layers of the fabric covering 60 rolled together and sutured in place, such as with stitches 78 seen in FIGS. 4A and 4B. Details of the process of forming the sewing tab 76 will be omitted for brevity, but those of skill in the art will understand that there are various ways to form such a tab.

At this stage, and as seen in FIGS. 5A and 5B, the lower length of the fabric covering 60 below the backstitch seam 74 will be severed at the fold line 70 (FIG. 3C) to form a first, outer tubular portion 82, and a second, inner tubular portion 84. As will be described, the tubular portions 82, 84 ultimately wrap around the ring-shaped insert 40 to form a sewing ring of the heart valve. In this regard, the outer tubular portion 82 is first inverted from its downward position around the inner tubular portion 84 into the upwardly-extending position shown in FIG. 5A surrounding the fabric-covered stent 80. Additionally, the backstitch seam 74 defines a circular line about which the sewing ring will pivot.

With reference to FIGS. 6A-6B, the aforementioned ring-shaped insert 40 is shown positioned around the fabric-covered stent 80, with the upper tubular fabric portion 82 interposed therebetween. As mentioned previously, the ring-shaped insert 40 includes a plurality of internal ribs 48, some of which extend radially. The cross-section shown in FIG. 6B is taken through one of these radial ribs 48 and illustrates a portion of the axially-extending inner wall 44 disposed substantially adjacent and parallel to the outer member 24 of the stent assembly 20 (with reference back to FIG. 1). The inner member 22 of the stent 24 is also shown juxtaposed against the outer member 24. The insert 40 therefore extends generally radially outward from the stent assembly 20, with two layers of the fabric covering 60 disposed therebetween. It should be noted that said two layers of fabric covering (one of which is a portion of the fabric covering encompassing the stent assembly 20, and one of which is the upper tubular portion 82) are not connected in the axial space between the stent assembly 20 and insert 40. Instead, the two layers of fabric covering extend underneath the stent assembly 20 and are joined together at the backstitch seam 74.

FIGS. 6A and 6B also illustrates an annular assembly fixture 90 having a tubular axial wall 92, and a radial flange 94 extending outward therefrom. The wall 92 is sized to fit closely adjacent the inner wall of the fabric-covered stent 80, while the flange 94 is positioned just below both the stent assembly 20 and insert 40, with one or more layers of the fabric covering 60 disposed therebetween. The fixture 90 causes the inner tubular portion 84 of the fabric covering 60 to bend outward at the backstitch seam 74 and presses it against the underside of the generally aligned stent assembly 20 and insert 40. Indeed, the combination of the sewing tab 76 and the fixture 90 axially positions the insert 40 with respect to the stent assembly 20. During assembly, the ring-shaped insert 40 is pushed upward against the sewing tab 76, and then the fixture 90 added to hold the insert in this preferred position. The combined length of the inner tubular portion 82 and outer tubular portion 84 of the fabric covering 60 is sufficient to encompass the insert 40, as will be explained below.

Figure 7A:
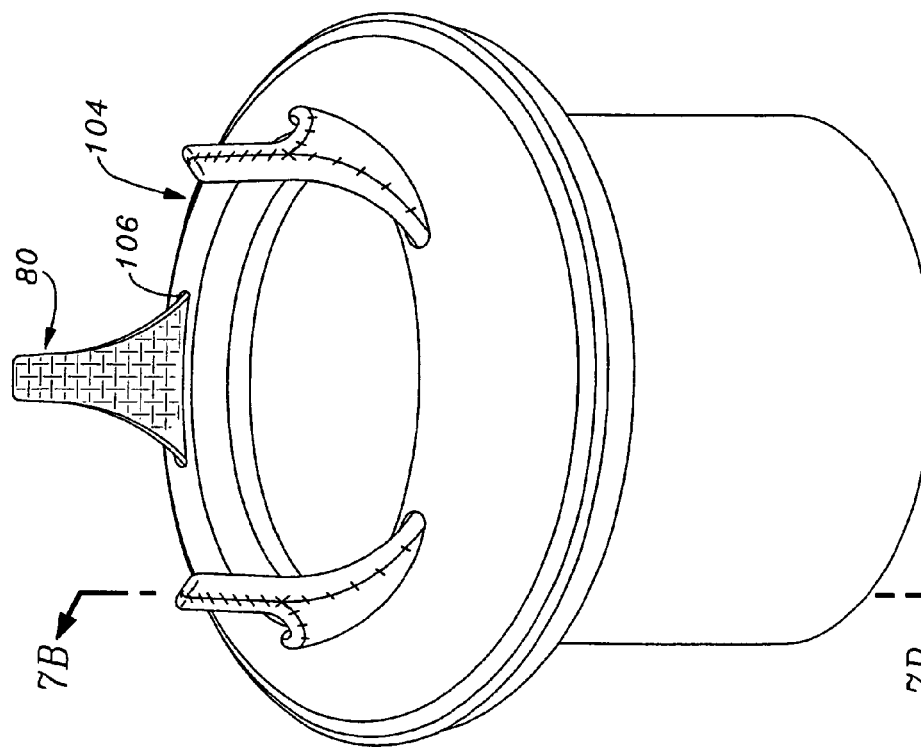
FIG. 7A is a perspective view of a further step in a heart valve assembly process wherein an outflow portion of the suture-permeable insert is covered with the help of a suturing fixture.
Figure 7B:
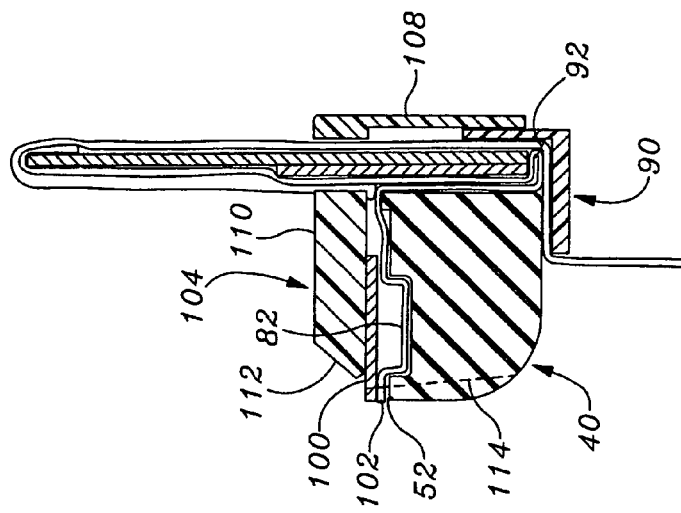
FIG. 7B is a cross-sectional view taken along line 7B-7B of FIG. 7A.

Now with reference to FIGS. 7A and 7B, a further step of adding a flat, suture-permeable ring 100 to the assembly of the heart valve is shown. First, the inner tubular portion 82 is folded outward to cover the outflow face 46 (FIG. 2) of the insert 40 and severed to form an edge 102 at the circular outer edge 52 of the insert. The suture-permeable ring 100 is then positioned on top of the tubular member 82, and a sewing fixture 104 is utilized to press the elements flat. The suture-permeable ring 100 stiffens the insert 40. That is, in a preferred embodiment, the insert 40 is silicone rubber, and the ring 100 is a stiff textile, preferably non-woven polyester. One particularly preferred material is sold under the trade name REMAY manufactured by Remay, Inc., Old Hickory, Tenn.

FIG. 7A illustrates the sewing fixture 104 in perspective, showing a plurality of apertures 106 that receive the commissure portions of the fabric-covered stent 80 projecting therethrough. The apertures 106 serve to center the annular sewing fixture 104 with respect to the fabric-covered stent 80 and insert 40. As seen in FIG. 7B, the sewing fixture 104 includes an inner axially extending wall 108 that fits just inside the axial wall 92 of the assembly fixture 90, and a radial flange 110 extending outward therefrom. The radial flange 110 has a tapered outer edge 112 that terminates short of the outer edge of the suture-permeable ring 100. As illustrated, the ring 100 is size such that its outer edge is aligned with the insert edge 52 and the edge 102 of the tubular portion 82. Consequently, a stitch 114 is passed around the circumference of the insert 40, joining the insert to both the tubular portion 82 and suture-permeable ring 100 at their respective outer edges. The sewing fixture 104 facilitates the stitching operation because the tapered outer edge 112 provides a clear circular guide. That is, the sewing fixture 110 maintains the respective elements sandwiched together (in conjunction with the assembly fixture 90), and exposes just a small peripheral portion of the ring 100 through which the fabricator passes the sewing needle. After this operation, the sewing fixture 104 is removed.

FIG. 7B also illustrates the arrangement of the fabric covering 60 around both the stent assembly 20 and the insert 40 at the commissure regions. In particular, the initial single piece of fabric is shown entirely encompassing the stent assembly 20, and partially encompassing the insert 40.

Figure 8B:
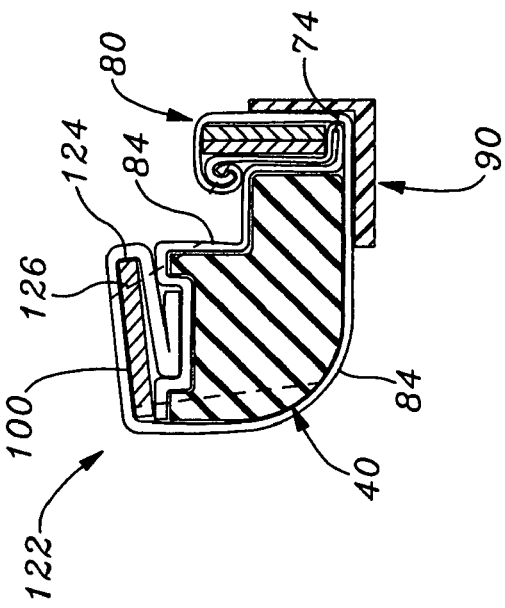
FIG. 8B is a cross-sectional view taken along line 8B-8B of FIG. 8A.
Figure 8A:
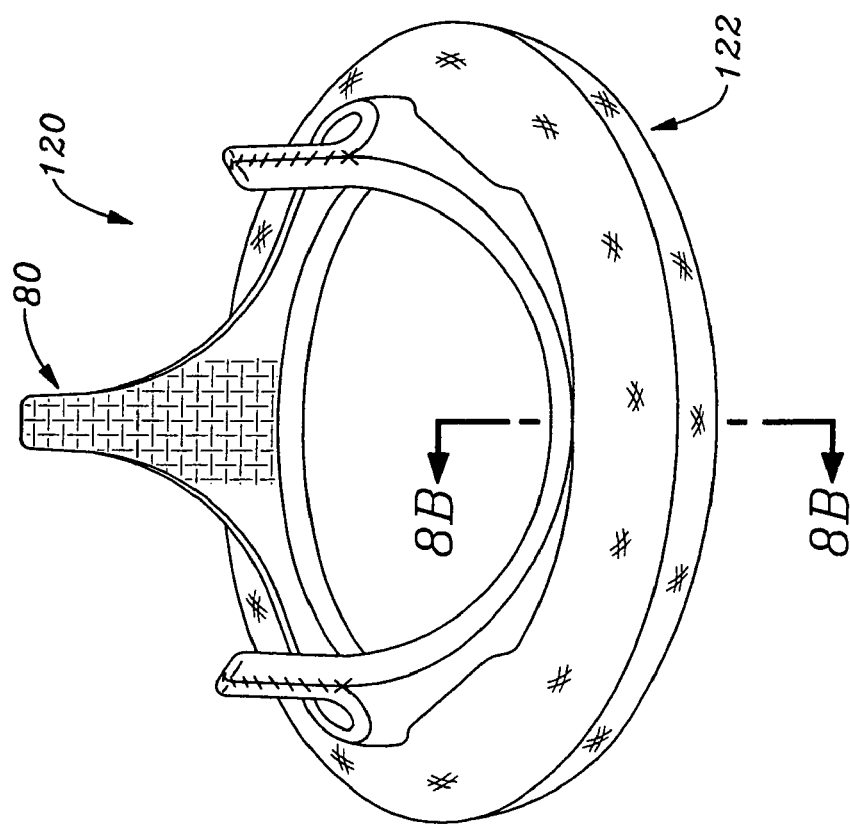
FIG. 8A is a perspective view of a subassembly of the heart valve of the present invention including the fabric-covered stent assembly and sewing ring.

FIGS. 8A and 8B illustrate a completed stent/sewing ring subassembly 120 comprising the cloth-covered stent 80 attached to the cloth-covered insert 40, or sewing ring 122. The inner tubular portion 84 of the cloth covering has been wrapped upward and inward around an inner edge 124 of the suture-permeable ring 100. The terminal end of the tubular portion 84 is folded or otherwise disposed within a recess formed by the recessed ribs 48 of the insert 40. To complete the sewing ring 122, a circular line of stitches 126 is provided through the tubular portion 84, inner edge of the ring 100, insert 40, and outer tubular portion 82. Again, the sewing ring 122 is exclusively attached to the fabric-covered stent 80 using the cloth covering 60, and specifically, the two components pivot with respect to one another about the backstitch seam 74. It should be noted that although the subassembly 120 is complete, the assembly fixture 90 remains in position for subsequent assembly steps.

Prior to attaching a wireform and tissue leaflets to the stent/sewing ring subassembly 120, an assembly handle 130 is introduced, as seen in FIGS. 9A and 9B. The handle 130 comprises a generally elongated grip 132 and a valve seat 134 rotatable dispose about one end. The valve seat 134 is mounted to rotate about an axis 136 that is angled with respect to the longitudinal axis of the elongated grip 132. The valve seat 134 has a stepped configuration with a base flange 138 and an upstanding cylinder 140. The stepped configuration of the valve seat 134 is sized to fit closely against the assembly fixture 90, as seen in FIG. 9B. As a result, the stent/sewing ring subassembly 120 can be rotatably mounted about one end of the handle 130 at an angle with respect to the grip 132.

Figure 10:
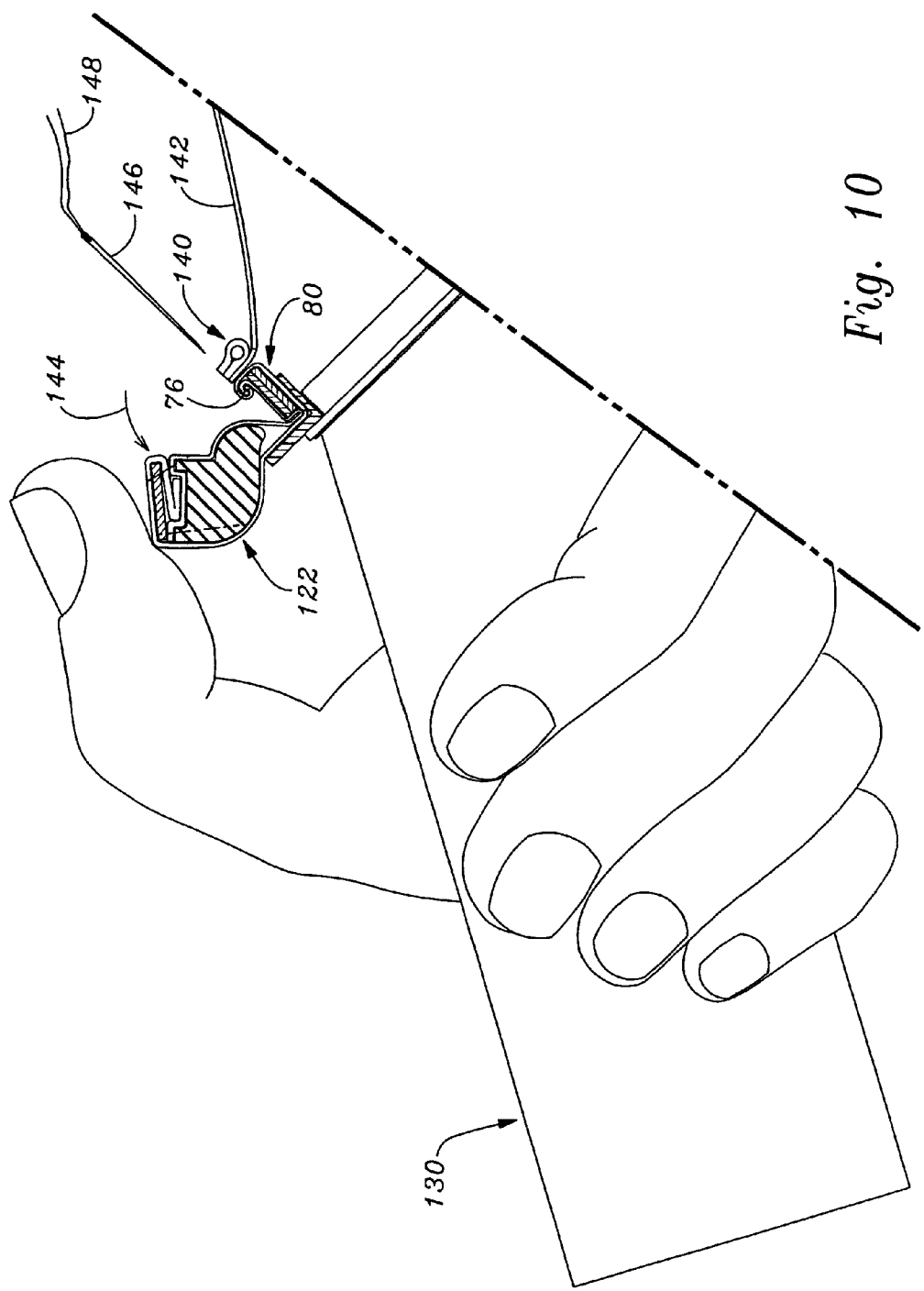
FIG. 10 is a partial sectional view of a step in the final assembly process wherein the sewing ring of the present invention pivots away from the stent assembly to facilitate suturing tissue valve leaflets and a wireform subassembly thereto.

FIG. 10 illustrates a further assembly step wherein a wireform subassembly 140 and a plurality of leaflets 142 are attached to the stent/sewing ring subassembly 120. Specifically, a fabricator grips the handle 130 and is able to pivot the sewing ring 122 radially outward from the fabric-covered stent 80, as seen by arrow 144, to facilitate manipulation of a needle 146 having thread 148 attached thereto. The needle 146 is used to form a stitch line (not shown) joining the wireform subassembly 140 to the fabric-covered stent 80, and specifically to the rolled fabric tab 76. Outer edges of the leaflets 142 are positioned between the stent 80 and wireform subassembly 140 such that the stitch line also passes therethrough. The flexible leaflets together provide the occluding surfaces of the valve.

Because of the ability to rotate the stent/sewing ring subassembly 120 about the angled handle 130, the same operation of pivoting the sewing ring 122 outward to facilitate formation of the stitch line can easily be performed around entire periphery of the heart valve. The outward pivoting of the sewing ring 122 results in greater visibility of the area in which the stitch line is formed, and reduces the chance of inadvertent puncture of components of the heart valve other than those intended.

Figure 11A:
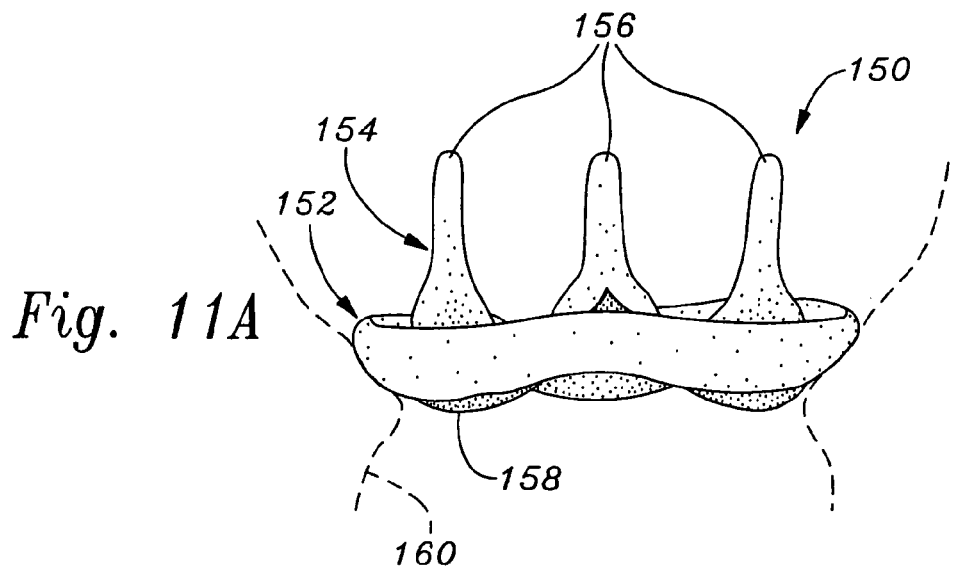
FIGS. 11A-11C are elevational views of a stent/sewing ring subassembly of an exemplary aortic or pulmonic heart valve of the present invention illustrating conversion of the sewing ring between two bi-stable positions.
Figure 11B:
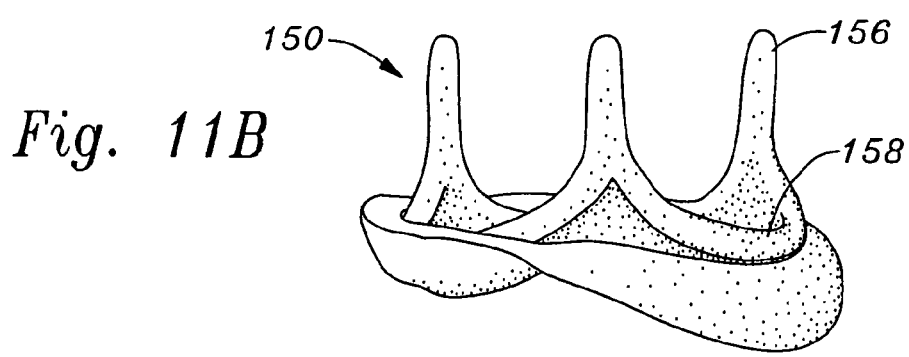
Figure 11C:
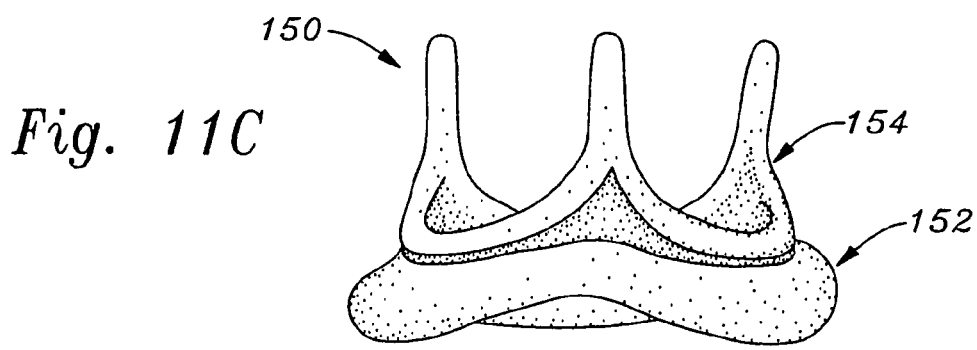

FIGS. 11A-11C illustrates an alternative stent/sewing ring subassembly 150 of the present invention in which a sewing ring 152 extends outward from a stent 154 and can be inverted from a position generally facing the inflow end of the subassembly (FIG. 11C), to a position generally facing the outflow end (FIG. 11A). As with the earlier described embodiment, the stent/sewing ring subassembly 150 includes a fabric covering that is desirably formed from a single piece of tubular fabric, as will be explained below. The stent 154 includes a plurality of upstanding commissure posts 156 extending toward the outflow end separated by cusp regions 158 that are convexly curved toward the inflow end. Although not shown in FIGS. 11A-11C, the stent 154 in conjunction with a wireform provides support for a plurality of flexible leaflets therebetween. The flexible leaflets together provide the occluding surfaces of the valve, and in a preferred embodiment are formed from bovine pericardial tissue.

Although the stent/sewing ring subassembly 150 can be used in a variety of positions within the heart, it is particularly useful in the aortic position which has a scalloped, three-dimensional configuration. The aortic valve is located at the outflow of the left ventricle, between the ventricle and the ascending aorta. Prosthetic aortic valves are typically sutured (or attached by other means) to the annulus tissue remaining after the defective host valve has been excised. The annulus tissue forms a tough, fibrous ledge extending inward from the surrounding anatomy to define a generally circular orifice between the ventricle and the ascending aorta. An exemplary implantation position for an aortic valve is illustrated in FIG. 11A, with a host annulus 160 indicated in dashed line. The stent/sewing ring subassembly 150 is also suitable for implant in the pulmonary position, which has a scalloped configuration, although such valve replacement procedures are less common.

A typical method of implantation includes passing a plurality of sutures through the prepared annulus prior to valve delivery. The suture lengths extend out of the surgical field and body and can thus be easily passed through the corresponding locations on the sewing ring, thus "attaching" the valve to the annulus. Subsequently, the valve is gently lowered along the array of sutures into position in contact with the annulus, and multiple knots formed securing each pair of suture lengths to the sewing ring. The ability to invert the sewing ring 152 into the position shown in FIG. 11C, generally extending toward the inflow end of the valve, provides a degree of separation of the sewing ring from the stent 154, and leaflets support thereby. As a result, the valve including the inverted sewing ring 152 as in FIG. 11C can be "attached" to the host annulus with a reduced risk of puncturing the fragile tissue leaflets. That is, the task of passing the sutures through the sewing ring is simplified because the sewing ring can be pivoted to extend away from the valve body and leaflets. Before or after contact with the annulus 160, the sewing ring 152 can be inverted as in FIG. 11B into the implantation position of FIG. 11A. Because the greatest axial forces on the aortic valve are during diastole from pressure built up on the outflow side of the valve, the valve will be forced against the annulus 160 and the sewing ring 152 will remain in the position of FIG. 11A.

FIGS. 12A-12D and 13A-13B illustrate various details of the stent/sewing ring assembly 150, and in particular the attachment configuration between the sewing ring 152 and stent 154. FIGS. 12A-12D are various views of a ring-shaped insert 160 that, in conjunction with a fabric covering 162 (FIGS. 13A-13B), defines the sewing ring 152.

As seen in the plan view of FIG. 12A, the insert 160 includes a circular outer edge 164 and an inner edge 166 having alternating regions of increased (168) and decreased (170) radial thickness, corresponding to the cusps and commissure regions, respectively, of the sewing ring 152 formed thereby. With reference to the cross-sectional views of FIGS. 12B and 12C, the insert 160 is primarily defined by a band that is angled outward to form a frustoconical shape. The outward angle θ of the band 172 is preferably in the range of about 20° and 45°, and more preferably is about 30°. The band 172 extends around the entire periphery of the insert 160, and a plurality of circular ribs 174 are provided on the outer face thereof. FIG. 12C illustrates the regions 168 of increased thickness, which are formed in the cusps of the sewing ring 152 by a curvilinear lower portion 176 and a plurality of upstanding walls 178. The regions of increased (168) and decreased (170) radial thickness help the sewing ring 152 invert from an orientation extending generally toward the outflow end of the valve and an orientation extending generally toward the inflow end. The walls 178 are seen in the plan view of FIG. 12A and define a celled structure. In a preferred embodiment, the insert 160 is molded from silicone rubber.

The insert 160 is shown in two configurations herein; a first configuration being shown in FIGS. 12C and 12D with an internal stiffening member 180 embedded within the band 172, and also within the thickened regions 168. In the second configuration, seen in FIGS. 13A and 13B, a stiffening member 182 that is separate from the insert 160 is provided, attached to the insert using the fabric covering 162. Both the embedded stiffening member 180 and the separate stiffening member 182 serve the same purpose, that is stiffening the relatively soft and flexible insert 160. The stiffening members 180 or 182 are relatively more stiff than the material of the insert 160, and may be made from a non-woven polyester.

Figure 13A:
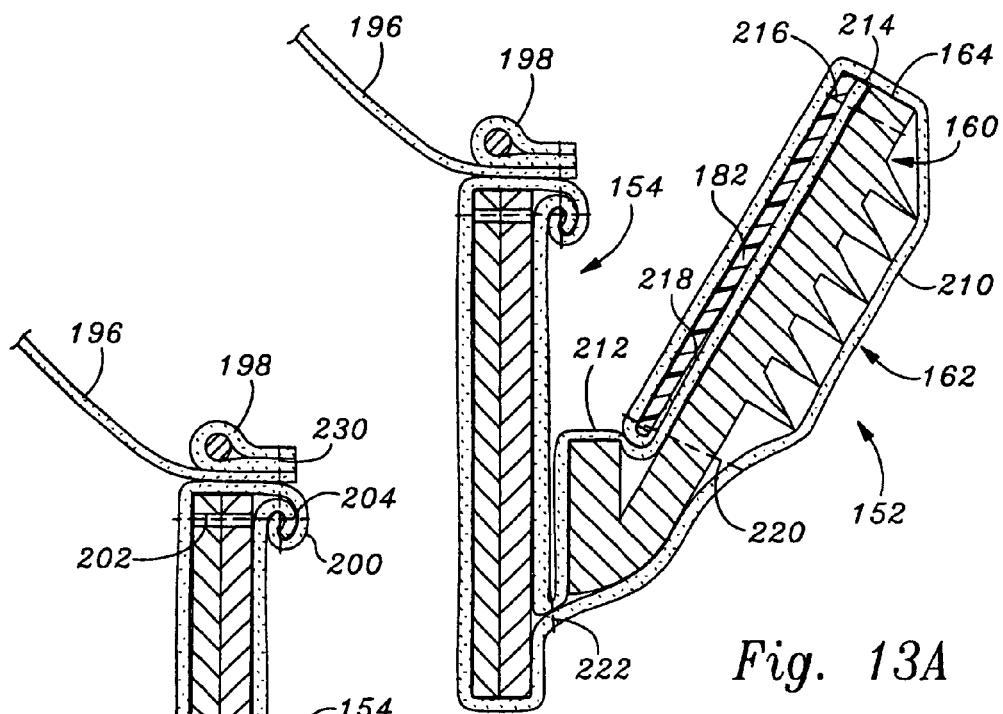
FIGS. 13A and 13B are cross-sectional views through the stent/sewing ring subassembly of FIGS. 11A-11C illustrating in more detail the sewing ring in the bi-stable positions.
Figure 13B:
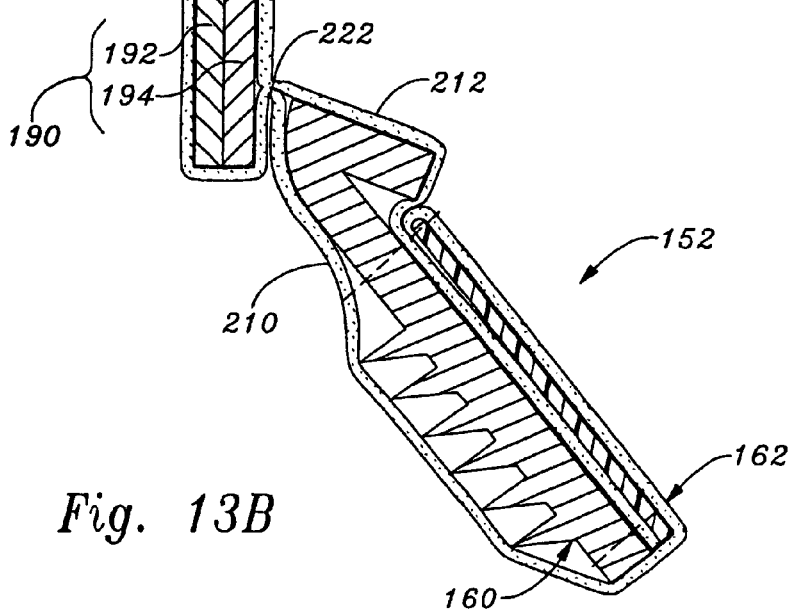

The other main components of the heart valve constructed using the stent/sewing ring subassembly 150 are illustrated in cross-section in FIGS. 13A and 13B. The valve includes a stent assembly 190 formed by a combination of an inner stent member 192 and an outer stent member 194, much like the members 22 and 24 illustrated in FIG. 1. The stent assembly 190 is encompassed by a fabric cover, preferably an extension of the fabric cover 162 around the sewing ring 152. A plurality of tissue leaflets 196 is secured to the outflow end of the stent 154 using a wireform subassembly 198. The overall shape of the heart valve is similar to the embodiment described earlier, as is evident from FIGS. 11A-11C.

As with the earlier embodiment, the fabric cover 162 is desirably formed from a single piece of tubular fabric. The assembly steps are similar to those described above for the first embodiment, and include wrapping the tubular fabric around the stent assembly 190 so that the free ends thereof can be joined together in a rolled sewing tab 200. In contrast to the earlier embodiment, the stent assembly 190 is provided with a plurality of through holes 202 extending in a line proximate the outflow edge thereof to enable passage of a stitch line 204 attaching the sewing tab 200 to the stent assembly. In particular, both the inner member 192 and outer member 194 include a plurality of through holes that are aligned for this purpose. The utility of this added stitch line 204 will become apparent below.

As with the first embodiment, the tubular fabric is severed to define two tubular portions that wrap around the insert 160 (and separate stiffening member 182 if provided) to form the sewing ring 152. In particular, an inner tubular portion 210 extends around the inflow side of the insert 160 and an outer tubular portion 212 extends around the outflow side. The outer tubular portion 212 covers the outflow face of the insert 160 and is severed at 214 at the circular outer edge 164. If a separate stiffening member 182 is used, as illustrated FIGS. 13A and 13B, a stitch line 216 secures it to the outer edges of the insert 160 and outer tubular portion 212. Otherwise, the stitch line 216 just secures the outer tubular portion 212 to the insert 160. The inner tubular portion 210 extends around the outer edge 164 and is secured to both the outer tubular portion 212 and insert 160 somewhere on the outflow face of the sewing ring. In the illustrated embodiment, where a separate stiffening member 182 is used, the inner tubular portion 210 wraps around the stiffening member and a free end 218 is trapped between the stiffening member and the outer tubular portion 212 and secured in that position using a line of stitches 220.

The sewing ring 152 pivots outward from the position generally adjacent the stent 154 shown in FIG. 13A to the position shown in FIG. 13B. The position shown in FIG. 13A corresponds to FIG. 11A, wherein the sewing ring 152 extends generally toward the outflow end of the valve, while the position shown in FIG. 13B corresponds to that shown in FIG. 11C, with the sewing ring extending generally toward the inflow end.

The only connection between the sewing ring 152 and the stent 154 is provided by the fabric cover 162 (i.e., there are no stitch lines between the insert 160 and the stent assembly 190, or fabric coverings thereon). The portions of the fabric covering 162 around the sewing ring 152 and stent 154 are distinguished at a seam 222, which provides a discrete pivot line (a point in cross-section) for the sewing ring. The seam 222 is located on the exterior of the stent 154, as opposed to being located on the inflow end of the stent, as was the case with the earlier described embodiment (see, e.g., FIG. 8B). Therefore, the sewing ring 152 pivots about the periphery of the stent 154.

The utility of the stitch line 204 connecting the rolled sewing tab 200 to stent assembly 190 will now be apparent. As the sewing ring 152 pivots between the position shown in FIG. 13A to the position shown in FIG. 13B, tension will be applied to the fabric cover 162 that tends to rotate the cover around the stent assembly 190 in a clockwise direction, from the perspective of the drawings. The stitch line 204 maintains the position of the rolled sewing tab 200 at the outflow end of the stent 154, and resists this tendency to rotate about the stent assembly 190.

Because of the novel connection between the sewing ring 152 and stent 154, the two positions shown in FIGS. 11A/13A and 11C/13B are bi-stable. Specifically, the band 172 of the insert 160 creates a generally frustoconical sewing ring 152 that can be inverted between orientations extending toward the outflow end and the inflow end. The resiliency of the insert 160 means that the outer circular edge 164 is stretched and placed in tension as it passes between the two positions, thus biasing the insert one way or the other. This bi-stable configuration greatly assists during both the manufacturing process, and the implantation procedure, as mentioned above. During manufacture, the fabric-covered stent/sewing ring subassembly 150 is constructed, and the tissue leaflets 196 and wireform assembly 198 are added. Because the sewing ring 152 can be pivoted away from the stent 154, attaching the leaflets 196 and wireform assembly 198 is simplified. That is, the suturing needle can more easily be passed through the various components to form the stitch line 230 when the sewing ring 154 is displaced out of the way. Various fixtures may be used during the assembly process as was described above with respect to the first embodiment.

As mentioned above, the particular shape of the insert 160 further facilitates inversion of the sewing ring 152 between the two stable positions. With reference back to FIG. 12A, the alternating radially thick (168) and thin (170) regions provide areas of varying bending strength in the insert 160. As a result, the cusp regions of the frustoconical band 172 can more easily be pivoted outward because of the thin regions 170 at the commissures, which present relatively little resistance to bending. Conversely, because of the thick regions 168, the insert 160 tends to snap between the two stable positions. That is, the thick regions 168 provide some rigidity to the structure.

Figure 14:
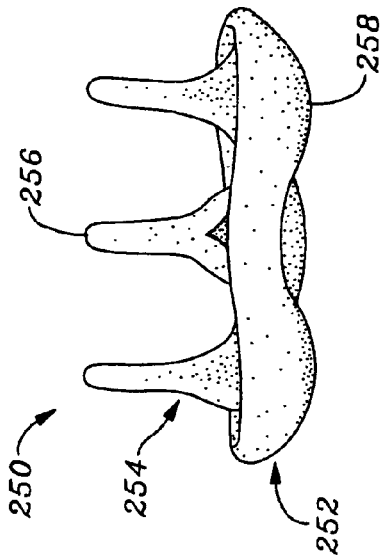
FIG. 14 is an elevational view of a stent/sewing ring subassembly of a further exemplary aortic or pulmonic heart valve of the present invention in a valve implant position of the sewing ring.

FIG. 14 illustrates a further exemplary stent/sewing ring subassembly 250 of the present invention in which a sewing ring 252 extends outward from a stent 254 and can be inverted from a position generally facing the inflow end of the subassembly, to the illustrated position shown, generally facing the outflow end. As with the earlier described embodiment, the stent/sewing ring subassembly 250 includes a fabric covering that is desirably formed from a single piece of tubular fabric. The stent 254 includes a plurality of upstanding commissure posts 256 extending toward the outflow end separated by cusp regions 258 that are convexly curved toward the inflow end. Although not shown in FIG. 14, the stent 254 in conjunction with a wireform provides support for a plurality of flexible leaflets therebetween. The flexible leaflets together provide the occluding surfaces of the valve. In a preferred embodiment, the flexible leaflets are formed from bovine pericardial tissue.

Figure 15C:
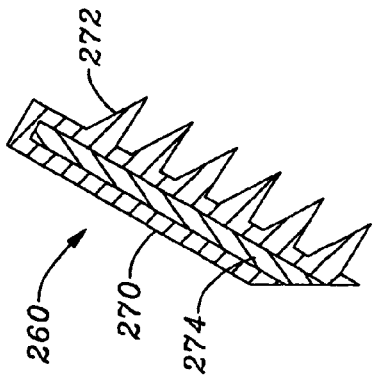
FIGS. 15A-15C are various views of a suture-permeable insert for the sewing ring of the subassembly seen in FIG. 14.
Figure 15A:
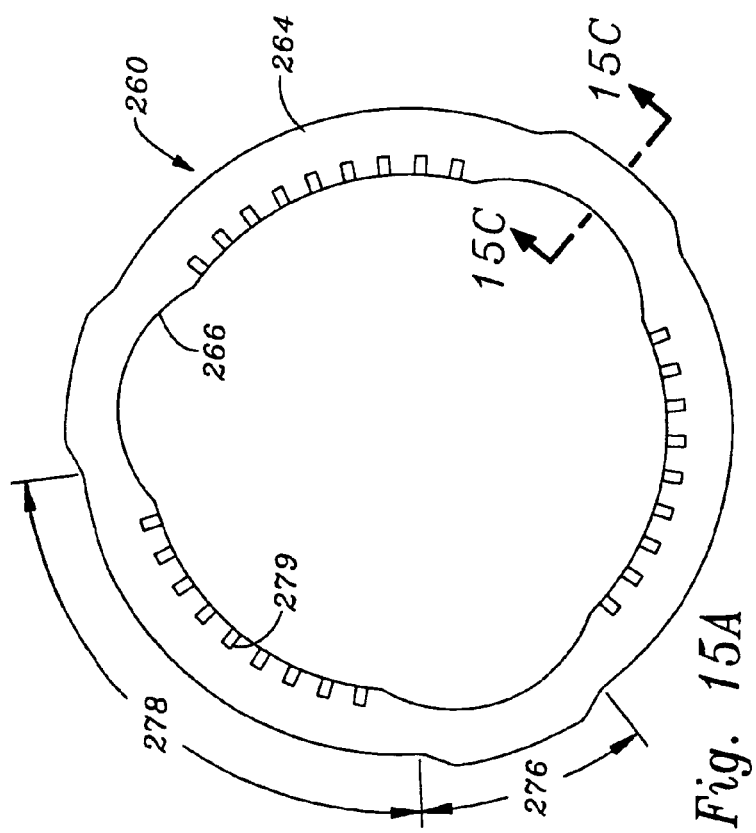
Figure 15B:
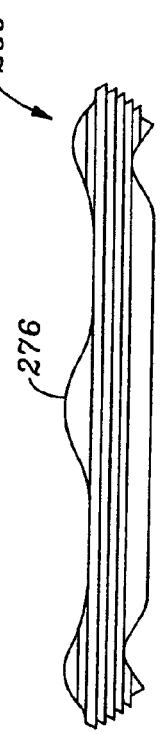

The stent/sewing ring subassembly 250 is in many ways similar to the subassembly 150 in FIGS. 11-13, but has a reduced size sewing ring insert 260 that provides distinct advantages. With reference to FIGS. 15A-15C, as seen prior to assembly in the subassembly 250, the insert 260 includes an undulating outer edge 264 and an undulating inner edge 266. With reference to the cross-sectional view of FIG. 15C taken through a commissure region, the insert 260 is defined by a band 270 that is angled outward to form a frustoconical shape and a plurality of outwardly extending ribs 272. There are no celled walls as in the previous embodiment, except for vestiges described below, and the radial dimension has been decreased from the version seen in FIGS. 12A-12C. Again, the outward angle of the band 270 is preferably in the range of about 20° and 45°, and more preferably is about 30°. The band 270 extends in a continuous fashion around entire periphery of the insert 260. An internal stiffening member 274 may optionally be embedded within the band 270. In a preferred embodiment, the insert 260 is molded from silicone rubber.

The outer edge 264 and inner edge 266 undulate in juxtaposition to form three commissure regions 276 extending radially outward from and separated by three cusp regions 278. The radial dimension of the exemplary insert 260 is generally constant around its circumference, although small reinforcing ribs 279 may be provided on the inside surface of the cusp regions 278 for stability during manipulation between inflow and outflow orientations. As with the earlier embodiment with varying thickness, the undulating shape of the insert 260 helps facilitate the pivoting inversion, and also helps the sewing ring 252 formed thereby conform to the scalloped (undulating) shape as seen in FIG. 14.

The insert 260 is seen in cross-section in FIGS. 16B and 17B assembled into a valve 280 having the stent/sewing ring subassembly 250. FIG. 16B shows the sewing ring 252 extending generally toward the inflow end of the valve, while FIG. 17B shows the sewing ring 252 extending generally toward the outflow end of the valve. These two positions are reflected in the elevational views of FIGS. 16A and 17A, which show two steps in a valve implantation procedure.

Prior to discussing the use, however, the structure of the stent/sewing ring subassembly 250 is somewhat modified from that shown in FIGS. 11-13. Specifically with reference to FIGS. 13A and 13B, the stent 154 is seen extending below the sewing ring on the inflow side of the valve. This arrangement is suitable for intra-annular placement (e.g., where a portion of the valve is within the annulus proper), but not suitable for supra-annular placement, where no portion of the valve is within the annulus. In contrast to the earlier embodiment, the valve 280 includes the sewing ring 252 attached at the inflow end of the stent 254 around the entire periphery thereof. As before, the sewing ring 252 attaches to the stent 254 at a seam line 282 at this inflow end. As a result, the sewing ring 252 pivots about the stent 254 along the seam line 282 (see FIGS. 16B and 17B).

Although the valve 280 having the stent/sewing ring subassembly 250 can be used in a variety of positions within the heart, it is particularly useful in either the aortic or pulmonic position which have a scalloped, three-dimensional configuration. Two steps in the implantation sequence illustrating the advantageous use of the sewing ring are shown in FIGS. 16A and 17A. Again, the positions of the sewing ring 252 in these two steps are shown in cross-section of the valve in FIGS. 16B and 17B.

Typically, a plurality of sutures 290 are passed through the annulus tissue 292 and extended out of the surgical field (and normally out of the patient's body as well). The sutures are grouped in interrupted pairs that will eventually be tied off at the sewing ring. Each pair of sutures is passed through the sewing ring 252 as shown, with the sewing ring in the outward pivoted configuration. In this way, the surgeon has greater access to the sewing ring 252 and there is less chance of puncturing a leaflet or other delicate valve structure. The valve 280 is seen attached to a conventional holder 294 at the distal end of a delivery handle 296.

Subsequently, as seen in FIG. 17A, the valve is gently guided along the array of pairs of sutures until the sewing ring 252 seats in contact with the annulus. In the illustrated embodiment, the sutures are positioned such that the valve 280 sits in the supra-annular position, not within the annulus proper. Prior to or as the valve 280 meets the annulus tissue 292, the sewing ring 252 pivots or converts back into the position seen in FIGS. 14 and 17B, generally extending toward the outflow end of the valve. The pairs of sutures 290 are then tied off at the sewing ring 252, as seen at 298. Again, backflow forces will simply force the valve against the annulus, and will not unduly stress the sutures or cause the sewing ring 252 to revert back to the implant orientation.

In a specific example of the advantages of the stent/sewing ring subassembly 250, a sewing ring 252 having a modified insert 260 sized for use with 21 mm diameter valves can be combined with a 23 mm valve. In other words, the pivoting action of the sewing ring 252 permits a smaller sewing ring to be used with a particular valve size with equal effectiveness as would be obtained with a conventional, larger sewing ring. Moreover, the valve orifice is increased for a lower pressure drop across the valve, and the small sewing ring 252 helps ensure that the coronary ostia are not occluded, which is often a worry in the supra-annular position.

The ability of the sewing rings of the present invention to pivot outward from the respective stents enables the resulting heart valve to have a larger orifice in comparison to earlier valves having the same outer diameter. This is a function of being able to pivot or invert the sewing ring outward during the implantation procedure. Because of this characteristic, the surgeon can more easily isolate the sewing ring with respect to the stent, and there is less likelihood of inadvertently puncturing one of the tissue leaflets, for example. The sewing ring can thus be made smaller in its radial dimension in comparison to earlier sewing rings, which could not pivot outward away from the stent. Such earlier sewing rings thus had to be made somewhat larger to give the surgeon a sufficient suturing platform away from the tissue leaflets. Because the sewing ring of the present invention can be made smaller, a larger valve orifice can be used for the same outer valve diameter.

Moreover, the ability to pivot the sewing rings of the current invention away from stent facilitates manufacture, as was clearly illustrated in FIG. 10. That is, the smallest valves have a diameter of about 19 mm, and the reader can appreciate that the sewing process for such a small valve is extremely exacting and time-consuming. Indeed, the stitching is typically performed under a magnifying glass. The present invention reduces the strain associated with such a detailed assembly process. The ability to effectively separate the sewing ring from the stent greatly increases the accessibility and visibility of the rolled sewing tab, for instance.

Finally, the present invention provides an extremely simplified construction of heart valve. That is, a single piece of tubular fabric is used to encompass both the stent and the sewing ring. The same tubular fabric forms the only connection between two components. Moreover, a minimum number of stitch lines are required, in contrast with earlier valves. With reference to FIG. 8B, the first embodiment requires a total of four stitch lines to encompass both the stent and sewing ring. The second embodiment, as seen in FIG. 13A, also requires a total of four stitch lines, in addition to a desirable fifth stitch line 204 to help prevent relative movement of the cloth around the stent assembly 190. In earlier tissue heart valves, additional stitch lines were required, thus increasing the assembly time and concurrent expense.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A sewing ring attached to a generally annular periphery of a prosthetic heart valve having an inflow end and an outflow end, comprising:
    a suture-permeable ring attached to the heart valve periphery and configured to pivot from a first position extending generally toward the outflow end of the valve to a second position extending generally toward the inflow end of the valve, wherein first and second positions are stable such that the sewing ring is bi-stable.

2. The sewing ring of claim 1, wherein the sewing ring comprises a suture-permeable insert ring and a fabric cover.

3. The sewing ring of claim 2, wherein the insert ring is substantially planar.

4. The sewing ring of claim 2, wherein the fabric covering the insert ring also covers a portion of the heart valve.

5. The sewing ring of claim 4, wherein the fabric covering both the insert ring and the portion of the heart valve also connects the ring to the heart valve periphery at a seam, and wherein the sewing ring pivots between the first and second positions about the seam.

6. The sewing ring of claim 1, wherein the suture-permeable ring is attached to the heart valve periphery along a line, and wherein the sewing ring pivots between the first and second positions about the line.

7. The sewing ring of claim 6, wherein the sewing ring comprises a suture-permeable insert ring and a fabric cover, and wherein the fabric covers the insert ring and connects the insert ring to the heart valve periphery at a seam, the seam defining the line about which the sewing ring pivots.

8. The sewing ring of claim 1, wherein the sewing ring includes a suture-permeable, generally frusto-conical insert ring and wherein the first and second positions correspond to the frusto-conical insert ring extending outward from the periphery in opposite axial directions.

9. The sewing ring of claim 8, wherein the insert ring includes alternating radially thick and thin regions facilitating pivoting of the sewing ring between the first and second positions.

10. The sewing ring of claim 8, wherein the insert ring has a radially undulating shape facilitating pivoting of the sewing ring between the first and second positions.

11. A prosthetic heart valve having an inflow end and an outflow end, comprising:
   a generally annular stent, and
   a suture-permeable sewing ring attached to a periphery of the stent so as to be moveable between two positions, wherein in the first position the sewing ring extends generally toward the outflow end of the valve and in the second position the sewing ring extends generally toward the inflow end of the valve, wherein first and second positions are stable such that the sewing ring is bi-stable.

12. The heart valve of claim 11, wherein the sewing ring comprises a suture-permeable insert ring and a fabric cover.

13. The heart valve of claim 12, wherein the fabric covering the insert ring also covers a portion of the stent.

14. The heart valve of claim 13, wherein a single piece of fabric is used to completely cover both the insert ring and the stent.

15. The heart valve of claim 11, wherein the sewing ring attaches to the stent exclusively with a portion of fabric that also covers at least a portion of the sewing ring.

16. The heart valve of claim 15, wherein a seam is provided in the fabric defining a line of attachment between the sewing ring and the stent, and wherein the sewing ring pivots about the seam between the first and second positions.

17. The heart valve of claim 11, wherein the suture-permeable sewing ring is attached to the stent periphery along a line, and wherein the sewing ring pivots between the first and second positions about the line.

18. The heart valve of claim 17, wherein the sewing ring comprises a suture-permeable insert ring and a fabric cover, and wherein the fabric covers the insert ring and connects the insert ring to the stent periphery at a seam, the seam defining the line about which the sewing ring pivots.

19. The heart valve of claim 11, wherein the sewing ring includes a suture-permeable, generally frusto-conical insert ring and wherein the first and second positions correspond to the frusto-conical insert ring extending toward the outflow end and the inflow end of the valve, respectively.

20. The heart valve of claim 19, wherein the insert ring includes alternating radially thick and thin regions facilitating movement of the sewing ring between the first and second positions.

21. The heart valve of claim 19, wherein the insert ring has a radially undulating shape facilitating pivoting of the sewing ring between the first and second positions.

* * * * *